United States Patent [19]

Ungpiyakul et al.

[11] Patent Number: 4,837,715

[45] Date of Patent: Jun. 6, 1989

[54] METHOD AND APPARATUS FOR DETECTING THE PLACEMENT OF COMPONENTS ON ABSORBENT ARTICLES

[75] Inventors: Tanakon Ungpiyakul; Arch D. Morgan; Thomas Douglas C., all of Neenah; Timothy J. Ketenhofen, Appleton; Douglas J. Marver, Mosinee; Laurie Couture-Dorschner, Hortonville; William S. Pomplun, Neenah, all of Wis.

[73] Assignee: Kimberly-Clark Corporation, Neenah, Wis.

[21] Appl. No.: 7,862

[22] Filed: Jan. 27, 1987

[51] Int. Cl.⁴ .................. G06F 15/20; G06F 15/46; G01N 21/84; B23Q 15/00
[52] U.S. Cl. .................................. 364/552; 364/469; 356/429; 83/74
[58] Field of Search ............... 364/552, 468, 469, 475, 364/470, 471; 356/429, 430, 431; 250/571, 572; 83/74, 358, 288; 156/522

[56] References Cited

U.S. PATENT DOCUMENTS

| | | | |
|---|---|---|---|
| 4,237,539 | 12/1980 | Piovoso et al. | 364/552 |
| 4,456,374 | 6/1984 | Langberg | 356/237 |
| 4,490,618 | 12/1984 | Cielo | 250/571 |
| 4,603,976 | 8/1986 | Fetzer et al. | 356/402 |
| 4,608,115 | 8/1986 | Schroth et al. | 156/519 |
| 4,680,205 | 7/1987 | Lerner et al. | 356/429 |
| 4,719,575 | 1/1988 | Gneuchtel | 364/469 |
| 4,757,930 | 7/1988 | Ditto | 83/74 |

FOREIGN PATENT DOCUMENTS

| | | |
|---|---|---|
| 3325126 | 1/1985 | Fed. Rep. of Germany . |
| 1575140 | 9/1980 | United Kingdom . |
| 2143320 | 2/1985 | United Kingdom . |
| 8402190 | 6/1984 | World Int. Prop. O. . |

Primary Examiner—Theodore M. Blum
Assistant Examiner—Gregory C. Issing
Attorney, Agent, or Firm—Paul Yee

[57] ABSTRACT

The present invention provides an apparatus for examining a moving web composed of an interconnected plurality of articles to determine a location of a selected component thereof. The apparatus includes an indicating mechanism for providing marker data corresponding to the presence of a selected article. A metering mechanism generates gauge data corresponding to selected incremental lengths along the article in the movement direction of the web. A designating mechanism provides reference data corresponding to a selected reference point on the article, and a locating mechanism detects position data corresponding to a position of a selected component of the article. An evaluating mechanism processes the reference data, location data and gauge data to determine a spaced distance between the component and the reference point. A comparator mechanism determines a difference between the spaced distance and a predetermined acceptance spacing range, and a culling mechanism designates selected articles for which the spaced distance is outside of the acceptance spacing range.

37 Claims, 18 Drawing Sheets

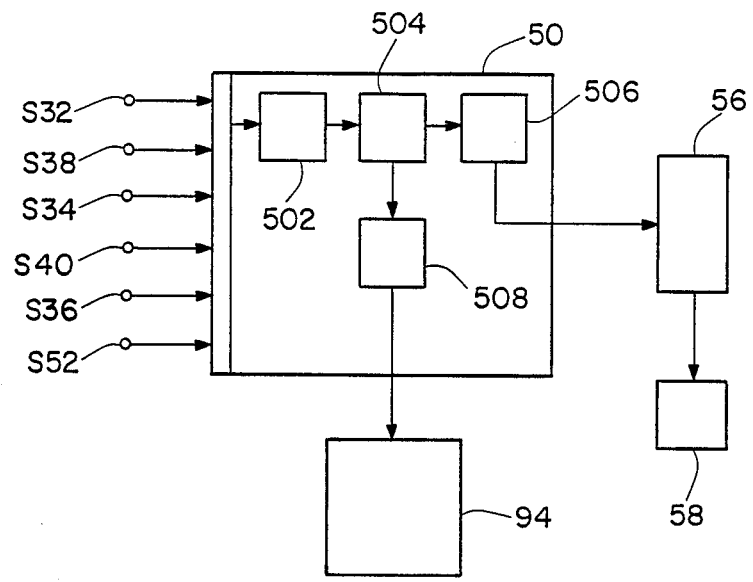
FIG. IA
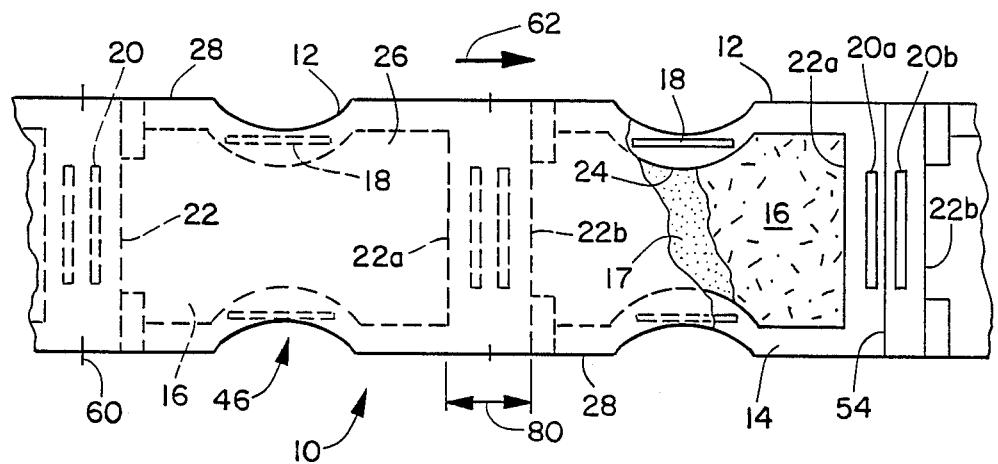
FIG. 2

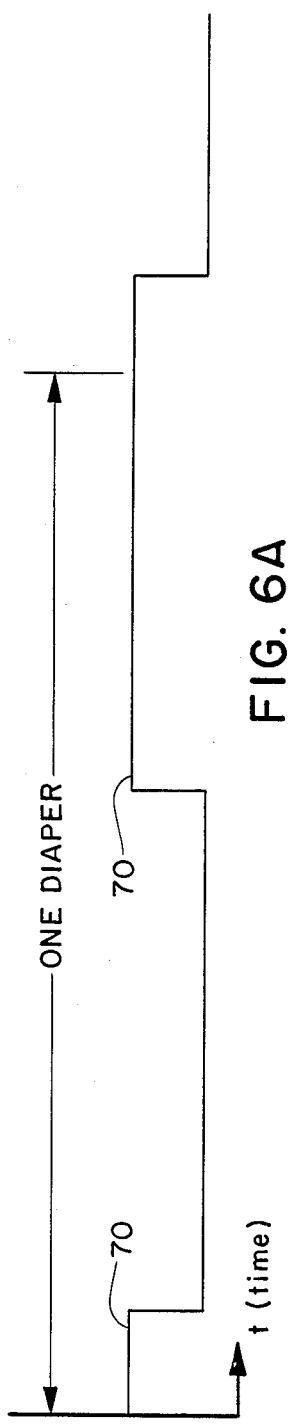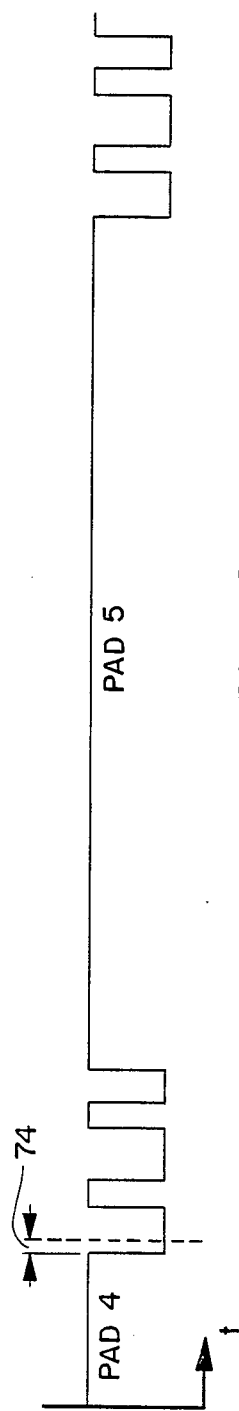

\* LESS THAN 1000 PHASE PULSE COUNTS

* LESS THAN 1000 PHASE PULSE COUNTS

METHOD AND APPARATUS FOR DETECTING THE PLACEMENT OF COMPONENTS ON ABSORBENT ARTICLES

FIELD OF THE INVENTION

The present invention relates to a method and apparatus for inspecting a moving web to determine the locations of selected component elements thereof. More particularly, the present invention relates to a method and apparatus for inspecting the locations of selected elastic members attached to an interconnected plurality of absorbent articles which comprise the web.

BACKGROUND OF THE INVENTION

Various photo/optical techniques have been employed to inspect the quality of moving webs. For example, PCT Application WO 84/02190 by J. Kuusi, published June 7, 1984, describes a procedure and means for nondestructively measuring the distribution of filler and/or coating materials in the thickness direction of paper or cardboard. Radiation from a radioisotope source is employed to excite characteristic X-ray radiation of a component of the material.

U.S. Pat. No. 4,456,374 issued June 26, 1984 to E. Langberg describes a method and apparatus for determining the presence or absence of a coating on a substrate. The technique involves placing the substrate into optical contact with a light guide and utilizing the principle of frustrated total internal reflection. Light scattered from the coating surface is monitored to indicate the presence of a coating.

U.S. Pat. No. 4,490,618 issued Dec. 25, 1984 to P. Cielo describes an apparatus for analyzing the surface of a fibrous web, such as a paper or a textile. The apparatus includes a prism structure, one surface of which is placed in contact with the fibrous web under a predetermined pressure. A collimated light beam is directed into the prism and light reflected from the contact surface through the prism is directed to a detector. The detector senses the light reflected by the contact surface as well as the light diffracted at the contact surface to indicate the surface condition of the fibrous web.

British Patent No. 1,575,140 published Sept. 17, 1980 and issued to Sick GmbH describes an electro-optical monitoring system for checking the presence of creases or other surface irregularities on a moving web of material. The monitoring apparatus directs a sharply defined light beam at a slightly skewed angle relative to a curved surface of the web. A photoelectric light detecting means detects light from the light beam to generate an output signal. The output signal changes in response to the entry of an irregularity into the light beam.

Conventional devices, such as those described above, have not been sufficiently effective for inspecting the registration and location of component elements on a moving web. Mispositioned or missing elements can degrade the quality of certain articles produced from the web. If the inspection system is ineffective, poor quality articles may not be efficiently or accurately culled and removed from the production lot. The alternative procedure of scrapping complete lots based on a limited sample inspection would be excessively wasteful and clearly undesirable. Conventional devices also have not been sufficiently effective for automatically adjusting the production process and machinery to keep all parameters within acceptance specifications. As a result, a production line may have to be stopped creating excessive downtime and reduced production efficiency.

BRIEF DESCRIPTION OF THE INVENTION

The present invention provides a distinctive method and apparatus for examining a moving web to determine a location of a selected component thereof. Generally stated the apparatus of the invention includes indicating means for providing marker data corresponding to the presence of a selected article portion of the web. Metering means generate gauge data corresponding to selected incremental lengths of the article along a movement direction of the web, and designating means provide reference data corresponding to a selected reference point on the article. Locating means detect position data corresponding to a position of a selected component of the article. Evaluating means process the reference data, the location data and the gauge data to determine a spaced distance between the component and the reference point. Comparator means determine a difference between the spaced distance and a predetermined acceptance spacing range, and culling means identify selected articles for which the spaced distance is outside of the acceptance spacing range.

The present invention further provides a distinctive method for examining a moving web composed of an interconnected plurality of articles to determine a location of a selected component thereof. The method comprises the steps of marking the presence of a selected article, and metering gauge data corresponding to selected incremental lengths along the article in the movement direction of the web. The method designates reference data corresponding to a selected reference point on the article, and senses position data corresponding to a location of a selected component of the article. The reference data, location data and gauge data are evaluated to measure a relative distance between the component and the reference point. The method compares the measured distance with a predetermined acceptance spacing range, and culls selected articles for which the measured distance is outside of the acceptance spacing range.

The present invention can efficiently inspect a web moving at high speed to ascertain the relative positional placements of selected component elements thereof. In particular, the invention can provide accurate, real-time information on each article during the production process, and individual articles can be selectively removed from a production lot. The quality of the production lot can be improved, and unnecessary waste can be reduced.

BRIEF DESCRIPTION OF THE DRAWINGS

The present invention will be more fully understood and further advantages will become apparent when reference is made to the following detailed description of the invention and the drawings, in which:

FIG. 1A representatively shows a schematic block diagram illustrating the relation between the computer and other elements of the invention;

FIG. 2 representatively shows a partially cut away top view of a web composed of an interconnected plurality of absorbent articles;

FIGS. 6A-F representatively show signal waveforms generated by the invention;

DETAILED DESCRIPTION OF THE INVENTION

Figure 1:
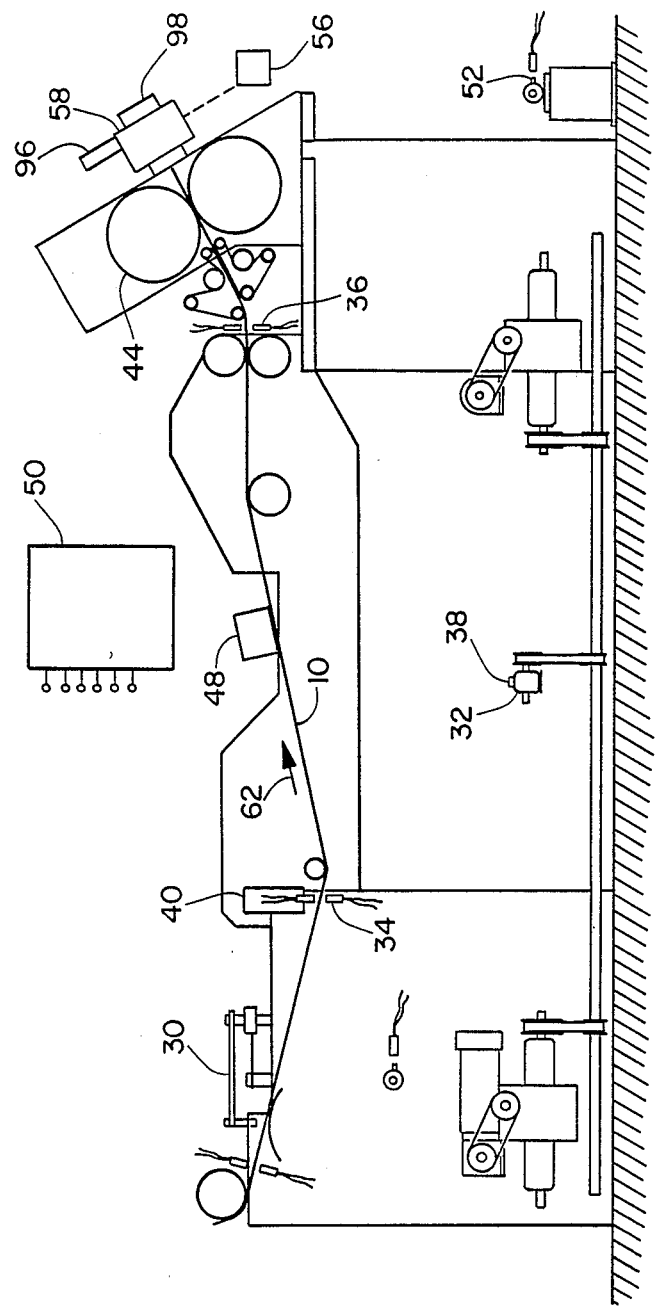
FIG. 1 representatively shows a schematic side view of an apparatus of the invention.

Referring to FIG. 1, the present invention provides an apparatus for examining a moving web 10, which includes an interconnected plurality of articles 12, to determine a location of a selected component thereof, such as cut edge or waist elastic members 20a-b (FIG. 2). Generally stated, the apparatus includes indicating means, such as pulse generator 32, for providing marker data corresponding to the presence and phase relation of a selected article 12 relative to other functional elements of the invention. Metering means, such as encoder pulse generator 38, generates gauge data corresponding to selected incremental lengths along article 12 in the movement direction 62 of web 10. Designating means, such as photoelectric detector 34, provide reference data corresponding to a selected reference point on article 12, and locating means, such as UV detector 40, provides position data corresponding to a location of a selected component of the article. Evaluating means, such as computer 50, processes the reference data, location data and gauge data to determine a spaced distance between the component element and the reference point. Comparator means, such as a portion of computer 50, determines a difference between the spaced distance and a predetermined acceptance spacing range. Culling means, such as a portion of computer 50, diverter mechanism 58 and programmable controller 56, automatically identify and remove selected articles for which the spaced distance is outside of the acceptance range.

In one aspect of the invention, the apparatus further includes second designating means, such as a photoelectric detector (photoeye) 36, for providing additional, updated reference data corresponding to the selected reference point on article 12. Second evaluating means, such as another portion of computer 50, processes the additional reference data along with the location data and gauge data to determine spacing data corresponding to a second relative position between the selected component and the reference point. Triggering means, such as cutoff proximity switch 52, produces signal data which can be correlated with individual separation points 54 produced in the web.

In another aspect of the invention, the locating means for detecting position data comprises an irradiating means for exposing the selected component to a source of UV radiation to induce an emission of a selected radiation spectra from the component. Receptor means then detect the emitted radiation spectra.

In yet another aspect of the invention, a registration control means automatically modifies a target set point to accurately locate selected components at predetermined positions on a moving web. Further aspects of the invention are described below.

For the purposes of the present description, the terms "data" and "signal" are to be interpreted in a general sense and are meant to designate various types of information produced during the operation of the invention. In particular, such types of information include, without limitation, information in the form of mechanical or electronic impulses.

The following detailed description will be made in the context of a web comprising an interconnected plurality of absorbent articles, such as disposable diapers, incontinence garments, sanitary napkins, and the like. It should be readily apparent, however, that the method and apparatus of the present invention may also be employed with other types of webs.

For the purposes of the present invention, the term "component" is intended to designate selected regions, such as cut edges and the like, as well as structural members, such as elastic strips and absorbent pads, comprising web 10 or article 12. Although the following detailed description is made in the context of determining the relative placements of elastic strips and absorbent pads, it is readily apparent that the method and apparatus of the invention can be employed to determine the relative locations of other components of web 10, such as patches, tabs, tapes and the like.

In the embodiment representatively shown in FIG. 2, web 10 comprises an interconnected plurality of disposable diaper articles 12. Web 10 is a composite web comprising a substantially liquid impermeable layer 14, such as a polyolefin film layer. For example, layer 14 may be composed of polyethylene, polypropylene or the like. A plurality of separate, absorbent bodies, such as absorbent pads 16, are superposed in facing relation with layer 14. Pads 16 are typically composed of a cellulosic material, such as airlaid wood pulp fluff. The pads may also comprise a coform material composed of an airlaid mixture of cellulosic fibers and synthetic polymer fibers. In addition, the pads may optionally include natural or synthetic superabsorbent materials, such as pectin, carboxymethyl cellulose, guar gum, polysaccharides, cross-linked synthetic polymers and the like. For example, polymers composed of alkali metal salts of lightly cross-linked polyacrylic acid have been found to be suitable superabsorbent materials. Each pad 16 can also include a tissue wrap 17 to increase the pad structural integrity. Pads 16 are substantially regularly spaced along the machine direction 62 of layer 14, and individual pads are separated by a discrete distance 80. Leg elastic members 18 are secured to layer 14 adjacent to lateral side edges 24 of each pad 16. In addition, waist elastic members 20 are secured to layer 14 adjacent to end edges 22 of the individual pads. A layer 26 of liquid permeable material, such as a spunbond nonwoven material, is superposed in facing relation with pads 16 and impervious layer 14. Thus, pad 16 and elastic members 18 and 20 are sandwiched between layers 14 and 26.

The various components of web 10 can be secured together by various suitable conventional techniques, such as adhesives, thermal bonding or sonic bonding. Typically, extruded lines or beads of hot melt adhesives are employed to secure the elastics to impermeable layer 14 and, optionally, to permeable layer 26. Such adhesives can be hot melt adhesives, pressure-sensitive adhesives, or the like. If desired, the adhesives may also be applied by conventional spray techniques. Similarly, adhesives can be employed to bond either or both of layers 14 and 26 to pad 16.

Preferably, side edges 28 of web 10 are contoured by removing selected sections. For example, cutting means, such as water cutter device 30, can be employed to cut away selected edge portions 46 corresponding to the leg openings of individual diaper articles.

It has been desirable to accurately inspect web 10 to assure uniform quality of the individual articles 12 formed from the web. Web 10 must be rapidly examined for missing components and for misplaced or misaligned components. Of particular interest are the relative placement between an individual pad 16 and its associated waist elastic members 20a-b, and the relative placement between the absorbent pads and the separation line 54 between articles 12. For example, the waist elastic members 20 may be missing or misaligned. In addition, the elastic waist member may be placed too close to the longitudinal end edges 22 of the pad or placed too close to the separation line 54. Also, the length of material between an individual end edge 22 and the separation line 54 may be too long or too short. If any one of these parameters does not meet predetermined acceptance criteria, it is desirable to identify and remove the individual out-of-specification diaper from the production lot. It is also desirable to automatically adjust the production process and apparatus to bring all parameters within accepted specification ranges. The distinctive apparatus and method of the present invention can advantageously improve the accuracy of the inspection process and can more effectively control the quality of the produced articles.

To accurately determine the locations of component parts and regions of web 10, the apparatus of the invention includes indicating means, such as line shaft encoder 32 representatively shown in FIG. 1. Encoder 32 provides marker pulse data corresponding to the position and presence of an individual selected article. The marker pulse data also corresponds to a particular position and phasing of the component elements of the invention relative to each other and relative to web 10. In the shown embodiment of the invention, the marker data has the form of electric impulse signals representatively shown in FIG. 6A. These electrical signals are routed through suitable electrical conductors S32 (FIG. 1A) to a computerized processing unit 50. A marker pulse 70 occurs one time per shaft revolution and is employed to obtain the phase relationship between the various electrical signals and the mechanical elements of the apparatus. Line shaft encoder 32 is connected to the drive mechanism (not shown) employed to move a conveyor which transports web 10 through the apparatus of the invention. Preferably, the connection is through an adjustable ratio gear box which can be selectively controlled such that substantially one encoder shaft revolution corresponds to the web length of one article 12.

A portion of the line shaft encoder further comprises metering means 38 for generating substantially regularly occurring phasing pulses 72 (FIG. 6B). The shown embodiment of the invention generates approximately 2000 phasing pulses per shaft revolution, and thus 2000 pulses per diaper article 12. These pulses are employed as a "ruler" to measure the phase and position relationships between the various electrical signals generated by the apparatus of the invention, and can be employed to develop desired measurements of the distances between selected components of web 10. In the shown embodiment of the invention, the phasing pulses are in the form of electrical signals, which are suitably directed to computer processing unit 50 through appropriate electrical conductors S38 (FIG. 1A).

Various suitable reference points on web 10 can be employed with the method and apparatus of the invention. For example, convenient, periodically occurring reference points are the longitudinally located end edges 22 of each of the individual pads 16. As representatively shown in FIG. 2, end edges 22 extend transversely along the cross direction 60 of web 10. Designating means, such as photoeye (PE) 34 observes web 10 as it passes thereby. Due to the optical contrast between those web portions containing pads 16 and the web portions between the pads, photoeye detector 34 can generate an electrical signal pulse corresponding to a leading pad edge 22a and a trailing pad edge 22b. These electrical signal pulses are directed to computer processor 50 through suitable wiring S34 (FIG. 1A).

In the manufacture of disposable diaper articles, the relative position between waist elastic members 20 and pads 16 has been important. The method and apparatus of the present invention can advantageously be configured to inspect the location of the waist elastic members. To accomplish this, a suitable locating means is employed to provide position data corresponding to the location of waist elastic members 20 on web 10.

Waist elastic members 20, however, are typically composed of a translucent film material, such as 3M KER 2210 or AFT CZ 9030B elastic film materials. The 3M material is composed of elastomer threads sandwiched between thermoplastic films by means of a hot embossing process, and is manufactured by 3M Company of Minneapolis, Minn. The AFT material is a coextruded film comprising a polyether block amide elastomer sandwiched between two skin layers composed of an ethylene vinyl acetate ionomer material, and is manufactured by Advanced Film Technologies, a division of James River Corporation located in Orange, Tex. Such materials may not be readily detected by conventional sensing mechanisms, such as photoelectric detectors, because of the lack of contrast between the waist elastic members and the remainder of the web. In particular, liner 26 may cover and obscure the elastic members. To address this situation, waist elastic members 20 are treated with brightening means, such as an optical brightener. Suitable optical brighteners include, for example, UVITEX O.B. manufactured by Ciba-Geigy, and LEUCOPURE EGM manufactured by Sandoz Chemicals Corporation. Other suitable optical brighteners include INTRA WITE O.B. manufactured by Crompton and Knowles, and PHORWITE K2002 manufactured by Mobay Chemical Company.

In a particular aspect of the invention, the optical brightener is sensitive to ultraviolet (UV) radiation. The optical brightener is capable of absorbing UV radiation and then fluorescing to emit visible light spectra that can be sensed by an optical detector. For the purposes of the present description, UV radiation is intended to designate electromagnetic radiation having wavelengths ranging from about 20–400 nm. In a preferred aspect of the invention, the locating means is provided by a UV activated detector 40 such as a SICK detector model LUT 1-4 available from SICK OPTIK ELEKTRONIK, INC. located in St. Paul, Minn.

Figure 3:
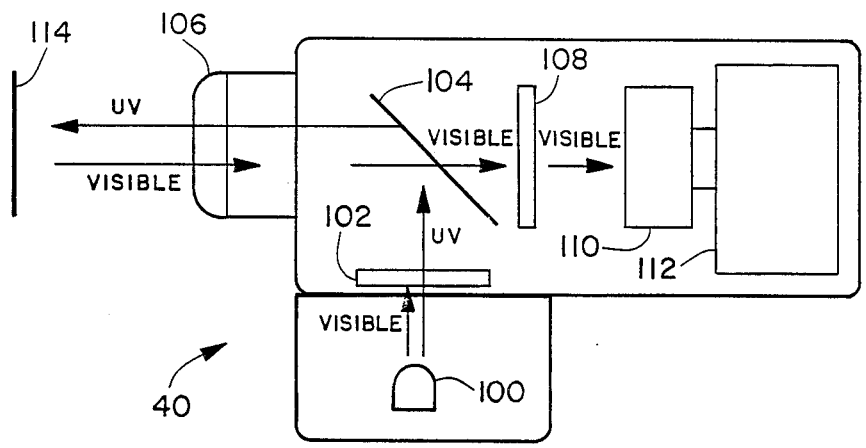
FIG. 3 representatively shows a schematic of a UV SICK detector.

Referring to FIG. 3, a suitable SICK detector employs a UV bulb 100 which is configured to emit modulated, or otherwise coded, visible and ultraviolet light. A bulb filter 102 substantially blocks the visible light spectra and allows selected UV light to pass through. The UV light has wavelengths of about 365 nm. A mirror 104 reflects the UV light to a lens 106, which concentrates the UV light into a small dot. In a particularly effective embodiment of the invention, lens 106 is a SICK Model 133 lens having a scanning range of about 47 mm. If a suitable, optically brightened target material 114 is present, the target will fluoresce and emit visible light near the focal point of lens 106. The visible light passes through lens 106 and through a partially silvered, filtering or otherwise partially reflective mirror 104. A lens filter 108 substantially blocks UV light but passes visible light. A detector element 110 senses the visible light and generates an output signal. An amplifier 112 within the detector electronics amplifies the output signal from the detector and selects out only the portion of the signal which is modulated. As a result, the amplifier can discriminate and reject extraneous, unmodulated signals, such as those caused by ambient natural light or fluorescent lights. The output from the amplifier preferably provides a digital signal ("on" or "off") which indicates whether or not there is an optically brightened material in front of lens 106.

Figure 4:
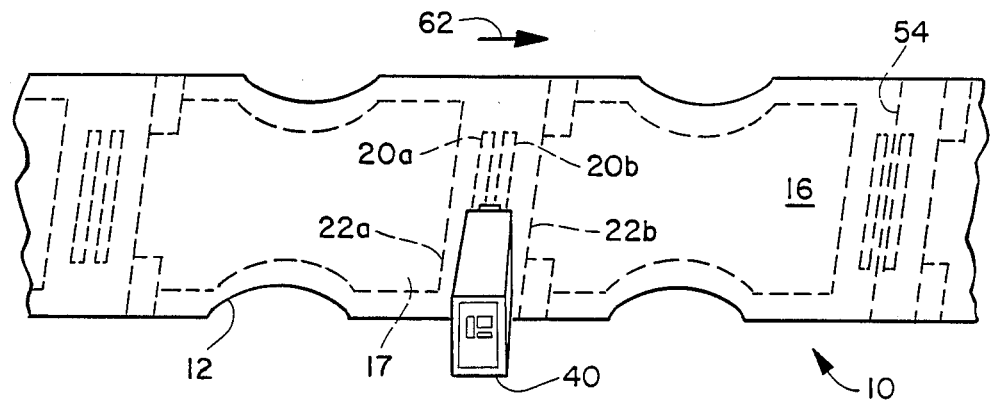
FIG. 4 representatively shows a UV detector positioned adjacent to a moving web.
Figure 5A:
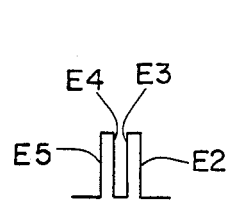
FIGS. 5A-B representatively show signal waveforms generated by the UV detector.

Referring to FIG. 4, UV detector 40 is suitably positioned adjacent web 10 to direct UV radiation toward the moving web and to receive visible light signals generated by particular web components. As web 10 passes by UV detector 40, the detector can sense four edges, E2–E5, as illustrated in FIG. 5A. The four edges correspond to two edges of waist elastic member 20a, and two edges of waist elastic 20b. Detector 40 generates corresponding electrical signals and passes them to computer 50 through suitable conductors S40 (FIG. 1A). The number of phasing pulses which are detected between the edges sensed by detector 40 provides desired position data corresponding to the relative locations between waist elastic members 20.

In a particular aspect of the invention, UV SICK detector 40 comprises at least a portion of the designating means for providing reference data corresponding to the leading and trailing edges of individual pads 16. In such embodiment of the invention, pads 16 are constructed and arranged to be activatable and detectable by irradiation with UV light. For example, tissue wrap 17 extending around each pad 16 can be treated with a suitable optical brightener, such as the optical brighteners previously discussed. With such arrangement, it is important that tissue wrap 17 extend closely proximate to the machine direction end edges 22a and 22b of pads 16 to ensure accurate designation and marking of these pad edges. Thus, UV detector 40 can be employed to generate the waveform information corresponding to both the positions of the pad end edges and the positions of the waist elastic members.

Figure 5B:
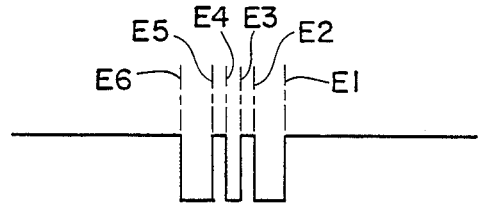

As web 10 passes by UV detector 40, the detector can sense six edges, E1–E6, as illustrated in FIG. 5B. The six edges correspond to the trailing end edge 22b of an absorbent pad, two edges of waist elastic member 20a, two edges of waist elastic 20b and the leading end edge 22a of the next successive absorbent pad. Detector 40 generates corresponding electrical signals and passes them to computer 50 through suitable conductors. The number of phasing pulses 72 occurring between the edges sensed by detector 40 provides desired position data corresponding to the relative locations between waist elastic members 20 and pad edge 22a and 22b.

Computer 50 includes evaluating means 502 (FIG. 1A) for processing reference data and location data, and for combining these data with gauge data to determine a relative, spaced distance between a selected component and a reference point. More particularly, computer 50 is employed to determine the relative distances between waist elastic members 20 and pad edges 22a and 22b. In addition, computer 50 can be employed to measure the relative position between separation line 54 and the end edges of consecutive pads 16. In the shown embodiment of the invention, computer 50 is a VME system comprising a FORCE SYS68K/CPU-1C, a FORCE SYS68K/SIO-1 serial I/O board, a FORCE SYS68K/SIO-1FP face panel, and three MIZAR VME-8305 parallel port boards. The FORCE components are available from Force Computers, Inc., Los Gatos, Calif. and the MIZAR components are available from Mizar, Inc., St. Paul, Minn.

Figure 8:
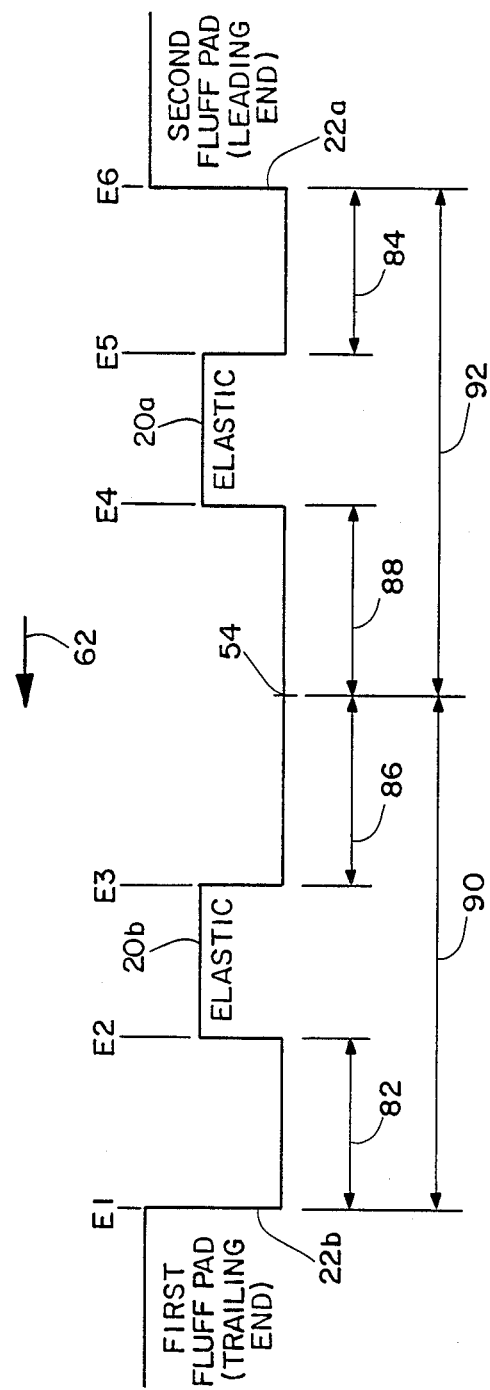
FIG. 8 representatively shows measurement data generated by the invention.

A final cutoff proximity switch 52 is employed to determine the position of the final separation or cutting line 54 (FIG. 8). This proximity switch generates a signal, such as an electrical pulse, which is employed to develop measurements corresponding to the trailing inset distance 86, the leading inset distance 88, the trailing end seal distance 90 and the leading end seal 92. These distances 86–92 are compared to predetermined acceptance ranges, and diaper articles having measurements falling outside of the acceptance ranges are culled and removed from the production lot.

Proximity switch 52, for example, can be a magnetic pickup switch device. Suitable proximity switches include TURCK Model BI5-G18-AN6X devices manufactured by Turck Inc., Minneapolis, Minn.

Proximity switch 52 is operatively coupled with a separating means for dividing web 10 into individual articles. In the shown embodiment illustrated in FIG. 1, the separating means comprises a rotary cutter 44. A proximity switch pulse signal is generated each time the cutter separates the web and is routed to computer 50 through suitable conductors S52 (FIG. 1A). The occurrence of the proximity switch signal may or may not correspond exactly with the occurrence of the cutting operation. As a result, an adjustment factor must be provided to computer 50 to allow an accurate determination of the precise position of cutting line 54 relative to other components of web 10. This adjustment or calibration factor is discussed in more detail below.

For improved operation, UV detector 40 is located as close as possible to cutter 44 to minimize any measurement errors introduced by any slipping, stretching or contracting of web 10 which might occur between the time detector 40 observes the web and the time that the web is cut. In the shown embodiment, however, the side edges 28 of web 10 are folded over toward the one longitudinal centerline of the web prior to the cutting operation by a folding mechanism 48. As a result, portions of the folded side edges can obscure and cover waist elastic members 20, and detector 40 must be spaced a longer distance away from cutter 44 at a position prior to the side folding operation.

Since moving web 10 undergoes drawing variations or changes in machine direction length due to slipping, stretching and contracting of the moving web, it has been useful to employ a second designating means, such as photoeye 36, to provide additional reference data corresponding to the end edges 22a and 22b of pads 16. In particular, photoeye 36 is selectively located closely adjacent to the position at which web 10 is cut or otherwise separated into individual diaper articles. At such position, photoeye 36 can sense the leading and trailing end edges of pads 16 and provide more accurate, updated reference data corresponding to the pad end edges 22a and 22b. The updated reference data is routed to computer 50 through signal conductors S36 (FIG. 1A)

In a particular aspect of the invention, UV detector 40 and photoeye detector 36 cooperate to provide a particularly effective designating means for providing updated reference data corresponding to the pad edge reference points on moving web 10. Second evaluating means, such as a selected portion of computer 50, processes the additional reference data, along with the location data and gauge data to determine more accurate, updated spacing data corresponding to the relative position between the waist elastic components and the pad end edge reference points. As a result, the method and apparatus of the invention can more accurately determine the placement of separation line 54 relative to the other components of the web, in particular, the position of the separation line relative to the pad edges 40 and relative to consecutive waist elastic members 20a and 20b.

As representatively shown in FIG. 1A, computer 50 includes comparator means 504 which receives the spacing data generated by evaluating means 502. The comparator means compares the spacing data with a predetermined acceptance spacing range, and sends an appropriate reject signal to computer culling means 506 if the spacing data is outside the acceptance range. In addition, computer comparator 504 sends appropriate signals to a waist elastic registration control loop 508. The waist elastic control loop portion of the computer is described in more detail below with reference to FIG. 1. The output from the control loop is then routed to a suitable regulating means 94 for adjusting the operation and phasing of an applicator which places the waist elastic members onto web 10.

With the shown embodiment of the invention, the culling means also comprises programmable controller 56 and diverter mechanism 58. The programmable controller receives instruction signals from computer 50, which identify defective articles. The controller uses the data to suitably direct diverter 58 to selectively route individual articles to either cull chute 96 or acceptance conveyor 98. Articles sent through the cull chute are discarded, and articles sent along the acceptance conveyor are routed for further processing, such as folding and packaging.

Figure 6D:
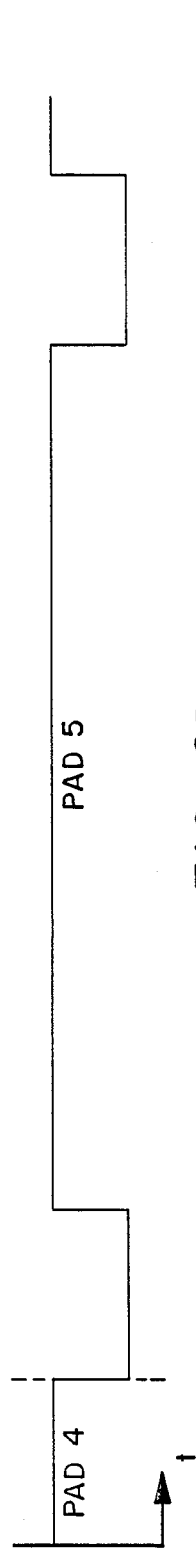

The various sensors and detectors comprising the present invention advantageously provide six basic sets of data, as representatively shown in FIGS. 6A–F. FIG. 6A illustrates a representative series of marker pulse signals. One marker pulse 70 is generated for each diaper article comprising web 10.

FIG. 6B representatively shows a series of encoder phase pulse signals 72 comprising the gauge data of the invention. In the illustrated embodiment, approximately 2000 encoder pulses occur for each diaper article, and it is readily apparent that the shown encoder pulses are exaggerated out of scale for the purposes of clarity.

FIG. 6C representatively shows signal pulses generated by UV detector 40, and FIG. 6D representatively shows signal pulses generated by photoeye 34. As illustrated in FIGS. 6C and 6D, there may be some difference 74 between the position of the trailing pad edge as sensed by UV detector 40 and the same edge as detected by photoeye 34.

Figure 6E:
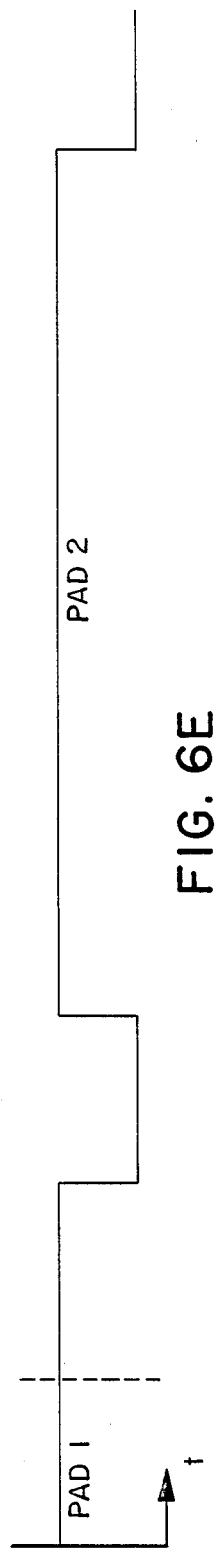

FIG. 6E representatively shows the signal pulse generated by the second photoeye 36. In the illustrated embodiment, photoeye 36 is located approximately 3.3 diapers removed from UV detector 40, and provides a signal which is shifted approximately 6600 pulses or counts relative to the pulse signals generated by UV detector 40.

Figure 6F:
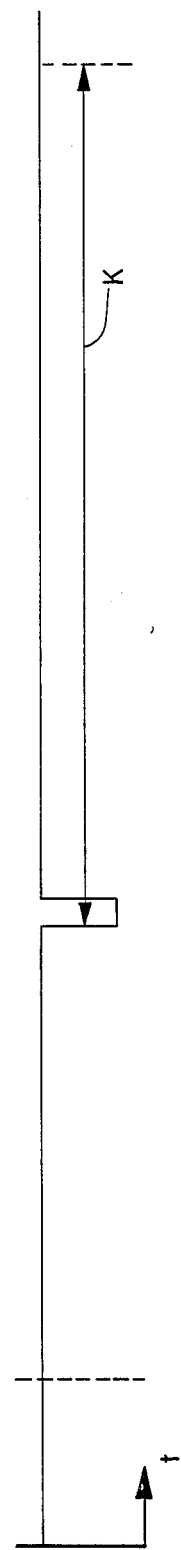

The final cutoff proximity switch signal is illustrated in FIG. 6F. A proximity switch signal is generated each time the cutter operates to divide the web into individual articles, but may not exactly coincide with the actual cutting operation. The actual cutting may occur a certain number of phasing pulses before or after the generation of the proximity switch signal. To compensate for this factor, computer 50 is empirically calibrated to selectively offset the proximity switch signal by a selected number of encoder phasing pulses to thereby generate shifted proximity switch data 68 (FIG. 7C). As a result, shifted proximity switch data 68 substantially corresponds to the actual location of separation line 54 relative to the other components of the web. The offset of the proximity switch signal is thus selectively adjusted to ensure that computer 50 is provided accurate data regarding the actual occurrence of a cutting of the web.

Figure 7A:
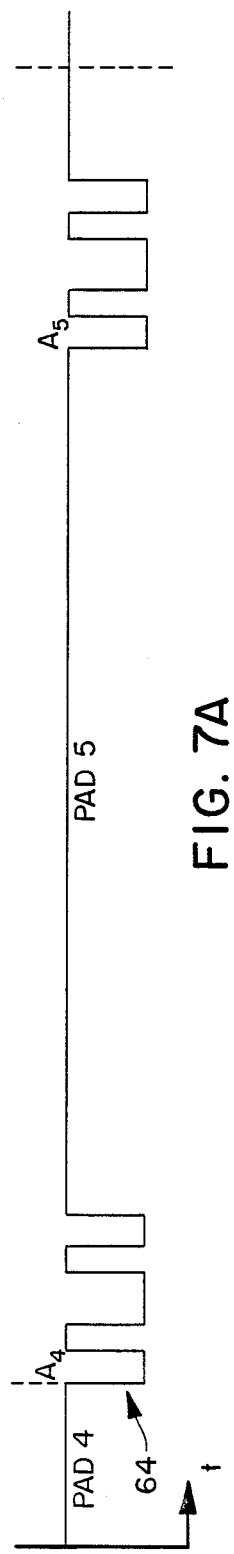
FIGS. 7A-C representatively show composite signal waveforms generated by the invention.
Figure 7B:
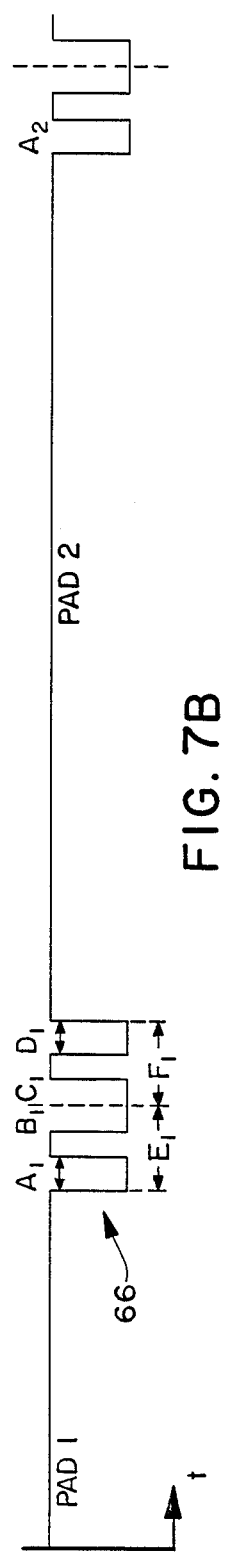
Figure 7C:
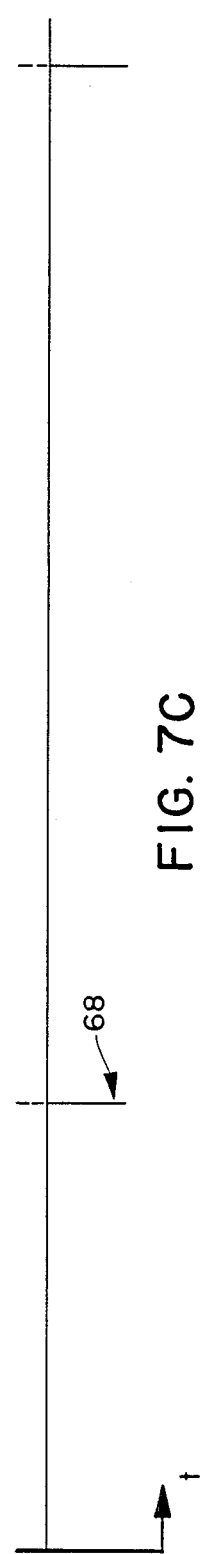

The above described six sets of data signals are employed to generate three composite signals, as representatively shown in FIGS. 7A–C. FIG. 7A illustrates composite position data 64 generated by "NAND-ing" pulse signals from photoeye 34 with pulse signals from UV detector 40. The resultant composite pulse signal provides more accurate position data regarding the relative placement between elastic members 20 and the pad end edges 22. Since the composite signal can thus more accurately represent the actual edge of the fluff pad, the use of the composite signal can reduce or remove errors generated by a situation in which the optically brightened wrap sheet is not exactly coincident with the fluff pad end edge.

FIG. 7B representatively shows shifted position pulse data 66. This signal corresponds to a combination of the updated reference data from photoeye detector 36 and the corresponding position data saved from UV detector 40. In this manner, information generated by photoeye 36 for a particular diaper is matched with corresponding information for the same diaper, which has been previously generated by UV detector 40 and saved by computer 50. For each diaper, there is a particular number of phasing pulses 72, or shift value, which occurs between the information generated by detector 40 and corresponding information generated by photoeye 36. Preferably, however, the actual shift values for a number of data sets are averaged by computer 50 to reduce the variability that may be introduced by photoeye 36. This averaged shift value is employed to correlate an updated reference pulse with its corresponding set of position pulse data from UV detector 40 and thereby generate the shifted position pulse data 66.

Shifted cutoff proximity switch data 68, representatively shown in FIG. 7C, is employed in combination with shifted position data 66 shown in FIG. 7B. These two signal data are employed to compute the distance between separation line 54 and waist elastic members 20, as well as the distance between separation line 54 and consecutively occurring leading and trailing pad end edges. This signal is generally identical to the final cutoff proximity switch data except that a phase shift value is added to the proximity switch data 52.

The actual shift value added to the proximity switch data 52 is established by a calibration procedure. During this calibration procedure, an operator determines the desired shift value and enters the value into computer 50. For example, the present invention can be calibrated employing the following procedure.

The operator first makes sure that the apparatus is running and that both end seal distances 90 and 92 (FIG. 8) are approximately equal with respect to separation line 54. The operator also observes web 10 to ensure that the waist elastic members 20 are, on the average, substantially centered within the end seal distances. The operator then keys computer 50, and the computer compares the final cutoff proximity switch signal 52 with the shifted composite position data 66. The computer averages information from fifty diaper articles to compute a shift value which will make a measured distance between cutoff line 54 and trailing pad edge 22b substantially equal to the measured distance between cutoff line 54 and the consecutively occurring leading pad edge 22a. This particular shift value will be held by computer 50 until the apparatus of the invention is recalibrated. A more detailed description of the computer calibration routine is set forth later in the specification.

The shown embodiment of the invention can be employed to develop the six measurements representatively shown in FIG. 8. The first measurement corresponds to a first spacing distance 82 between pad trailing edge 22b and trailing edge waist elastic member 20b. The second measurement corresponds to a second spacing distance 84 between pad leading edge 22a and leading edge waist elastic member 20a. The third measurement corresponds to a trailing inset distance 86 between trailing edge waist elastic 20b and separation line 54. The fourth measurement corresponds to a leading inset distance 88 between leading waist elastic member 20a and separation line 54. The fifth measurement corresponds to trailing end seal length 90 between trailing pad edge 22b and separation line 54. The sixth measurement corresponds to a leading end seal length 92 between pad leading edge 22a and separation line 54.

A suitable comparator means compares various measured distances with selected, corresponding acceptance value ranges. For example, the comparator means can comprise a part of computer 50, and can be configured to compare trailing end seal length 90 to an acceptance value range. If end seal 90 is too short, a reject signal can be generated to cull the particular, unacceptable article from the production lot. Similarly, any of the other measured lengths and distances can be compared to corresponding acceptance value ranges, and appropriate signals can be generated to direct mechanisms, such as programmable controller 56 and diverter 58, to cull individual, unacceptable articles from the production lot.

It should be noted that, in the shown embodiment, two readily available utilities are the line shaft encoder phasing pulse counter, and a task signal that is periodically activated. In the shown embodiment of the invention, this task signal is activated every 10 milliseconds. The line shaft encoder signal is connected to a counter within computer 50, and the value of the counter decreases by one each time a falling edge of the signal occurs. With the illustrated embodiment, the counter value is employed for measurement, and the 10 millisecond task function is employed to trigger cull operations and to detect irregularities in the signals generated by the invention.

Figure 9A:
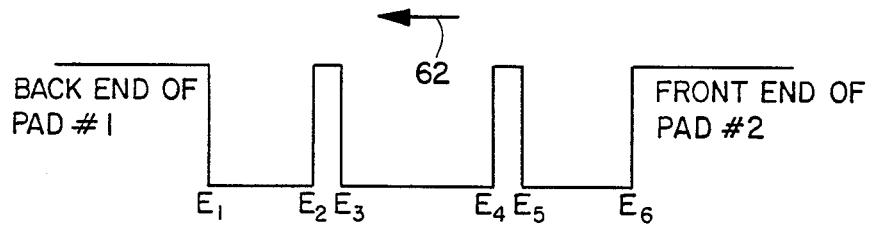
FIGS. 9A-D representatively show signal waveforms generated by defective articles.

Referring to the UV detector signal illustrated in FIG. 9A, E1 represents the trailing end edge of a fluff pad, E2-E3 represent the trailing waist elastic member, E4-E5 represent the leading waist elastic member and E6 represents the leading end edge of the next consecutive pad. The measurement objective is to locate edges E1 through E6 in the units of the line shaft encoder counts. Once these values are obtained and combined with the proximity switch data, defects in the placement of the waist elastics and the end seal lengths 90 and 92 can be detected.

Figure 9B:
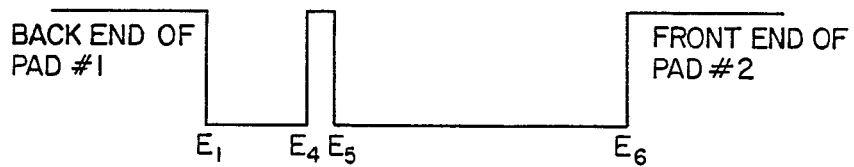
Figure 9C:
Figure 9D:

FIG. 9A representatively shows a representative signal detected when the waist elastic members are correctly registered. If one of the waist elastic members is missing or misplaced, the signal waveform from the UV detector can look like FIGS. 9B. If a waist elastic becomes partially placed on pad 16, the signal may look as representatively shown in FIG. 9C. When both tapes are missing or misplaced, the signal will be similar to FIG. 9D. Each of the fault situations should be detected to provide a high reliability system. Substantially no defective diapers should be allowed to remain in the production lot, and substantially all of the acceptable articles should be retained in the production lot.

Another consideration is that the detection system may produce a noisy signal; i.e. more than six detected edges per article. This situation may be due to actual electrical noises or to process problems, such as an area within the pad which is deficient of material or a pad which has ragged edges. Both conditions are detected to ensure high reliability within the system.

An article tracking scheme is employed to generate shifted position signal 66 (FIG. 7B). In the shown embodiment of the invention, this tracking scheme employs two assumptions. The first assumption is that the separation between UV detector 40 and photoeye 36 can be precisely determined. The second assumption is that the phase between the UV detector 40 and the final cutoff proximity switch signal 52 will not change more than one-half article. On the basis of these assumptions, edge E1 can be tracked as follows. Signals corresponding to edges E1 through E6 are stored in a circular buffer within computer 50 each time the signals are obtained. For each signal from photoeye 36, the buffer is searched for an edge signal E1 that is within one-half article of the specified separation (about 1000 shaft encoder pulses) from that photoeye signal. The corresponding edge that can be found is employed to calculate trailing inset distance 86, leading inset distance 88, trailing end seal length 90 and leading end seal length 92. If a corresponding E1 edge can not be found, the computer logic will determine that the UV signal is missing and that the diaper should be culled.

Four cull outputs can be generated by the inspection aspect of the cull routine. The first output is generated when spacing distance 82 or spacing distance 84 is less than a specified minimum limit. Such a situation can occur if one of the waist elastic members is too close to the absorbent pad. The second output is generated when trailing inset distance 86 or leading inset distance 88 is less than a specified minimum limit. Such a condition occurs when either one of the end seal distances is too short. The third cull output is generated when trailing end seal length 90 or leading end seal length 92 is less than a minimum limit, and the fourth cull output is generated when one or more of the six required edges is missing; i.e. if less than six edges are detected.

In one embodiment of the invention, the cull output is normally "off", and the cull sub-routine turns it "on" when a defective article is detected. Alternatively, as employed in the illustrated embodiment, the cull output is arranged to be normally "on" and then turned "off" when an acceptable article is detected. This second method technique can provide several advantages. In particular, articles will be culled if the hardware fails, signals are missing, or if the computer software cannot keep up with the apparatus machine speed.

It should be noted that spurious signals within the system may produce an inaccurate operation of the invention. For example, the signal associated with a defective article may contain two or four edges. If such a signal is corrupted with one or two noise pulses, it may resemble a good signal and allow a defective article to go undetected. Certain reasonableness checks are employed to help protect against this phenomenon. In particular, the following rules can be employed in the design of the system for detecting edges E1-E6.

a. A valid signal must have six edges per article.
b. All six edges must occur within a phase period corresponding to one-half an article. In other words, a signal edges more than one-half article away from a first edges is processed with the data corresponding to the next consecutive article.
c. A separation between two consecutive rising (or falling) edges cannot be less than the preselected width of a waist elastic member.
d. Since a digital signal has only two states, there cannot be two successive rising edges or two successive falling edges.
e. The separations E2-E3 and E4-E5 correspond to the widths of the waist elastic members. Thus, they must fall within a predetermined range. Similarly, the separation E3-E4 must also fall within another specified range because it is a predetermined spacing between consecutively occurring waist elastic members.

Figure 10:
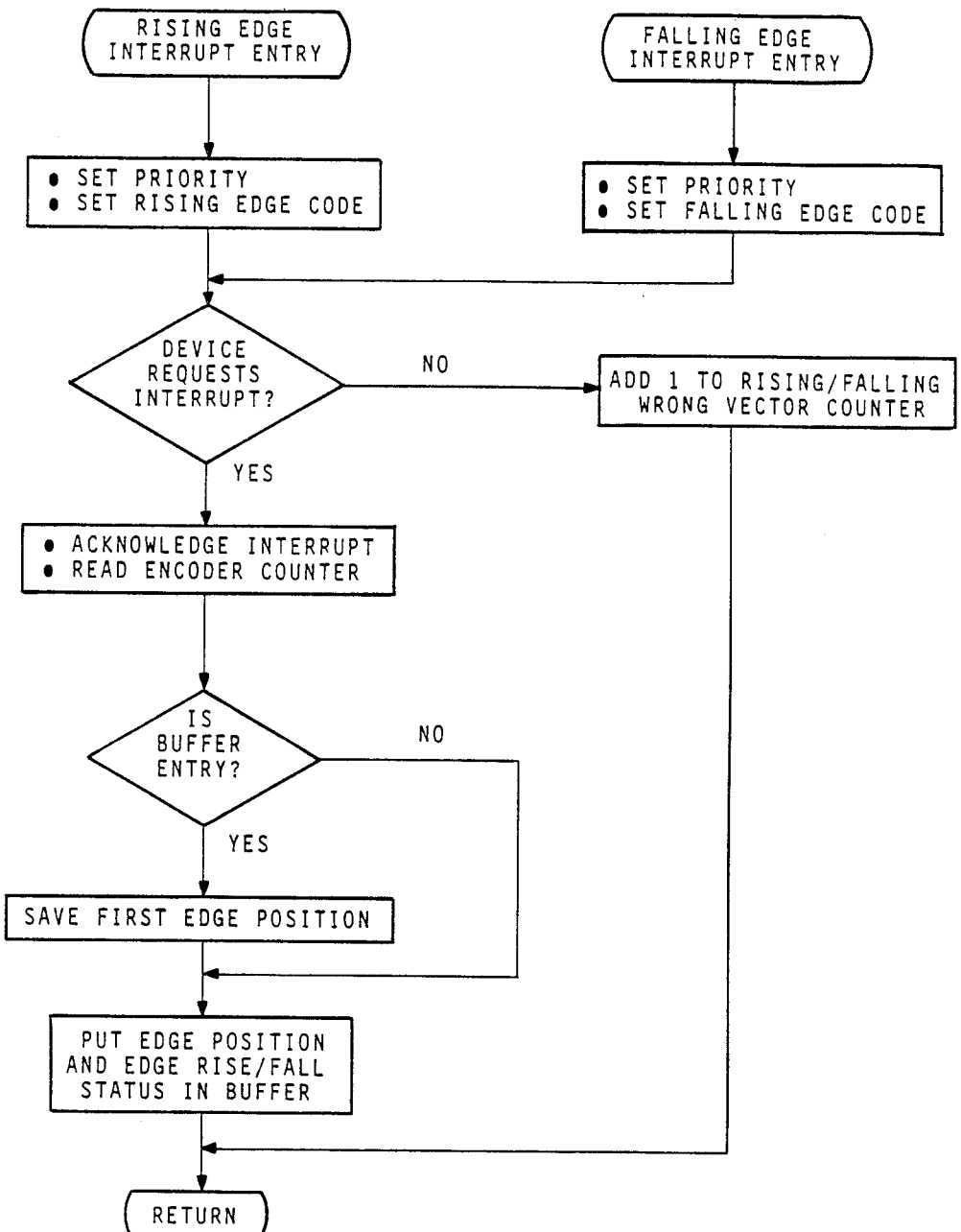
FIG. 10 representatively shows a block flow diagram for the interrupt service routine of the invention.

On the basis of the above rules, particularly rule (e), the edge detection scheme employed by the shown embodiment of the invention is configured to employ three separate tasks. The first task is an interrupt service routine with at least one entry point. For example, the entry point may correspond to either a rising edge interrupt vector triggered by a rising signal level from detector 40, or a falling edge interrupt vector triggered by falling signal level from the detector. Preferably, however, the first task has two different entry points to provide faster operation and to allow a wider choice of useable hardware. One of the entry points is the rising edge interrupt vector and the other entry point is the falling edge interrupt vector, as representatively shown in FIG. 10. The rising edge interrupt vector and the falling edge interrupt vector are numbers corresponding to particular address points at which to begin desired program routines. This interrupt service routine then checks whether or not the interrupting device, such as UV detector 40, has requested the interrupt. If not, it is concluded that the vector is improperly generated, and the task is terminated. If the vector is properly generated, the routine checks to determine whether the interrupt is the first for the current article. If so, the encoder counter position of this first edge is saved. All edges including their rising/falling status are stored in a first-in-first-out (FIFO) circular buffer.

Figure 11:
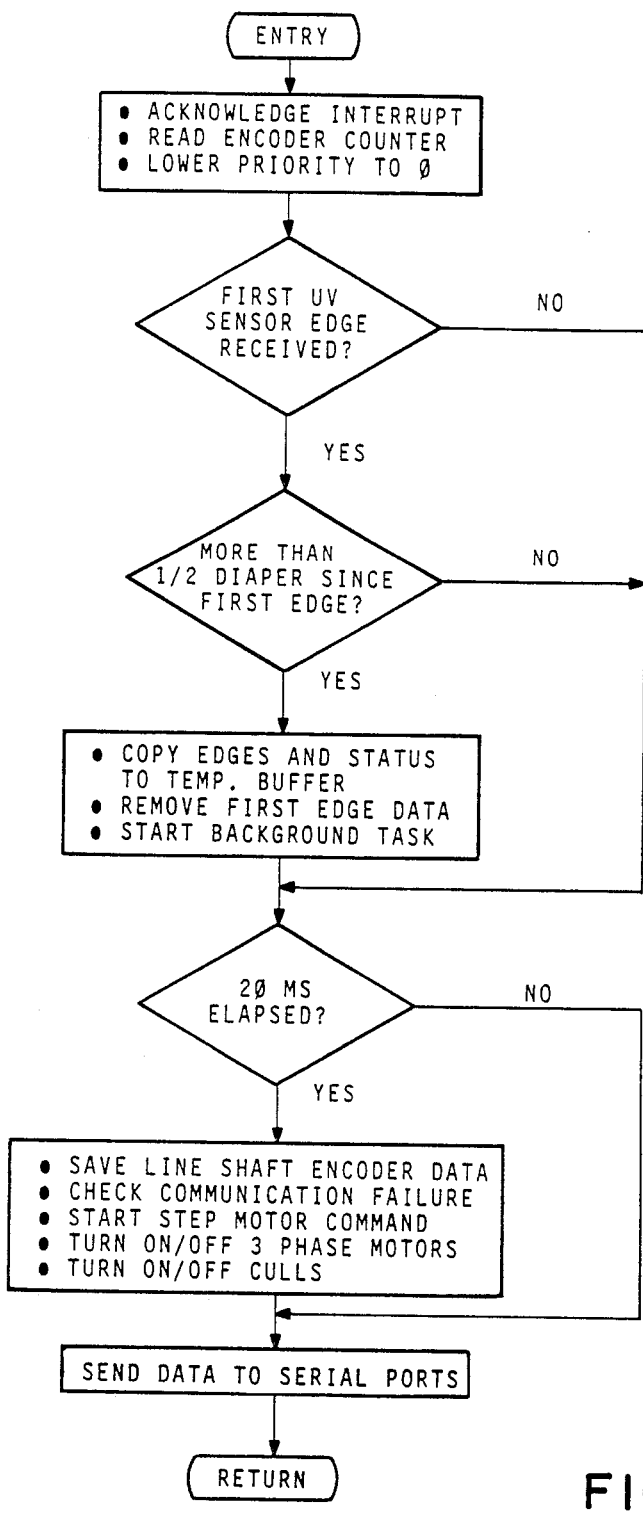
FIG. 11 representatively shows a block flow diagram for a task check routine of the invention.

The second task is a checking task to determine whether the first edge E1 of an article has been received. A block diagram of a suitable checking task function is illustrated in FIG. 11. In the shown embodiment, this checking task is provided by the 10 millisecond task check function within the system. If the first edge of an article has not been received, the checking task is skipped. However, if the first edge of an article has been received, the device of the invention checks whether the machine position has become more than one-half article away from this first edge. If this second check is "true", the FIFO circular buffer is signaled to empty the information contained therein into a temporary buffer to be employed to the third task described below. This ends the article data gathering function, and an edge detected after this event will be considered to be the first edge of the next consecutive article.

The third task is an analyzing task which removes data from the temporary buffer filled by the checking task and performs the following: First, the analyzing task tries to locate the waist elastic widths corresponding to the separations between E2 and E3 and between E4 and E5. If no corresponding tape widths are found, the article is determined to be irregular and a signal is generated to cull the article. If the edges corresponding to E2 through E5 are found, edge E1 is then defined as the edge immediately proceeding edge E2, and edge E6 is defined as the edge immediately following edge E5. Other edges, if any, are ignored. A flow chart illustrating this routine is representatively shown in FIG. 12.

After the edge detection data is processed, computer 50 places the data in a storage buffer. A timer routine then copies the data from the storage buffer into a working buffer and starts a UV detector data processing routine.

Figure 12:
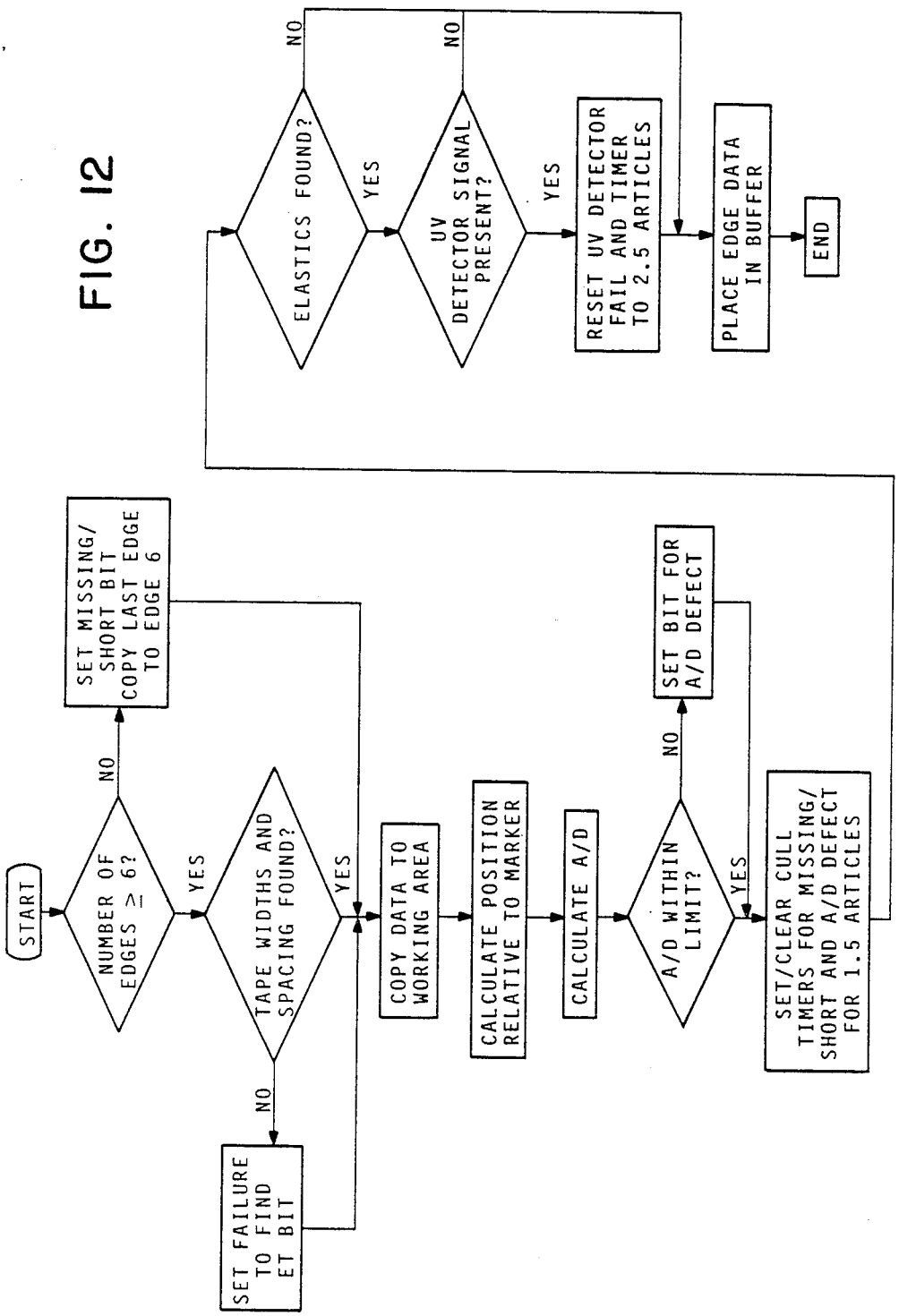
FIG. 12 representatively shows a block flow diagram for a task routine which validates UV detector signals and defines the trailing and leading edges of a pad.

A flow diagram of the data processing routine is representatively shown in FIG. 12. In the shown embodiment, the routine checks the signal integrity and generates a cull signal if it determines that waist elastic members are missing or misplaced. The routine also calculates "A" and "D" (FIG. 7B). "A" and "D" correspond to the number of encoder counts occurring between pad 16 and a corresponding, adjacently located waist elastic member 20. If "A" and "D" are within predetermined limits, the culled output signal is turned "off" for a phase period corresponding to approximately 1.5 articles (about 3000 encoder counts). In addition, the cull output signal corresponding to a failure of the UV detector is turned "off" for a phase period corresponding to approximately 2.5 articles (5000 encoder counts). The processed UV detector data is placed in a buffer for use in a final cutoff photoeye data processing routine and a final cutoff proximity data processing routine.

Figure 13:
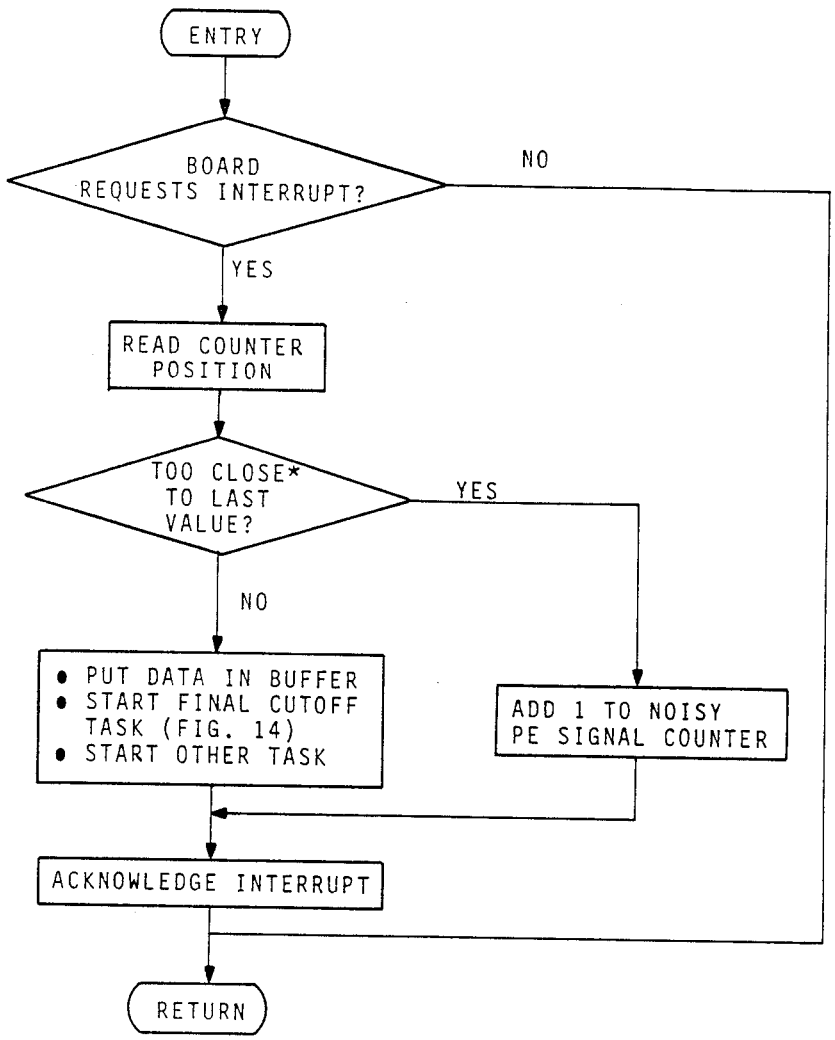
FIG. 13 is a flow diagram which representatively shows a final cutoff photoeye interrupt service routine.

A representative flow diagram of a final cutoff photoeye interrupt service routine is shown in FIG. 13. In the illustrated embodiment, the interrupt routine reads gauge data represented by the number of phasing pulses recorded by a phase pulse counter. The routine checks for spurious pulses, and places the processed data into a buffer for use in the final cutoff photoeye data processing routine.

Figure 14:
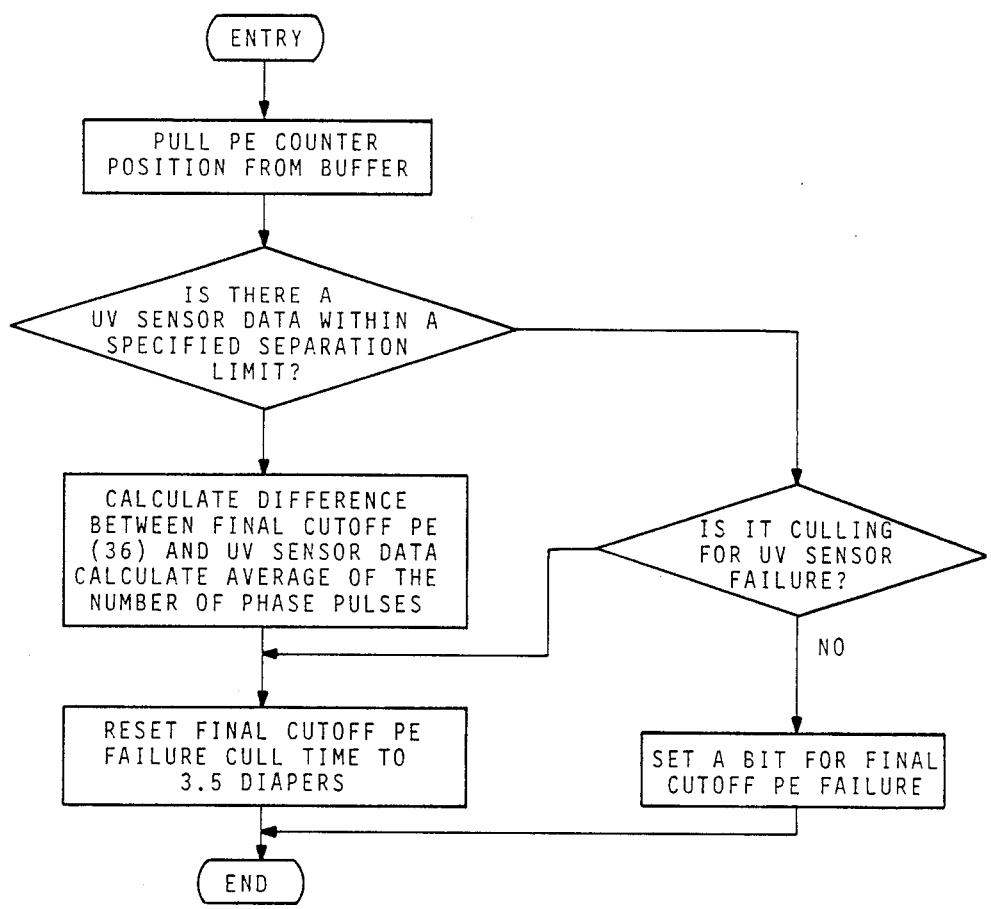
FIG. 14 is a flow diagram which representatively shows a final cutoff photoeye data processing routine.

A flow diagram of a representative final cutoff photoeye data processing routine is shown is FIG. 14. In the illustrated embodiment, the processing routine matches data from photoeye (PE) 36 with data from the UV detector 40. The routine calculates the phase separation; e.g., number of phase pulses; between the data from UV detector 40 and the data from photoeye 36, and also calculates an average separation value.

Figure 15:
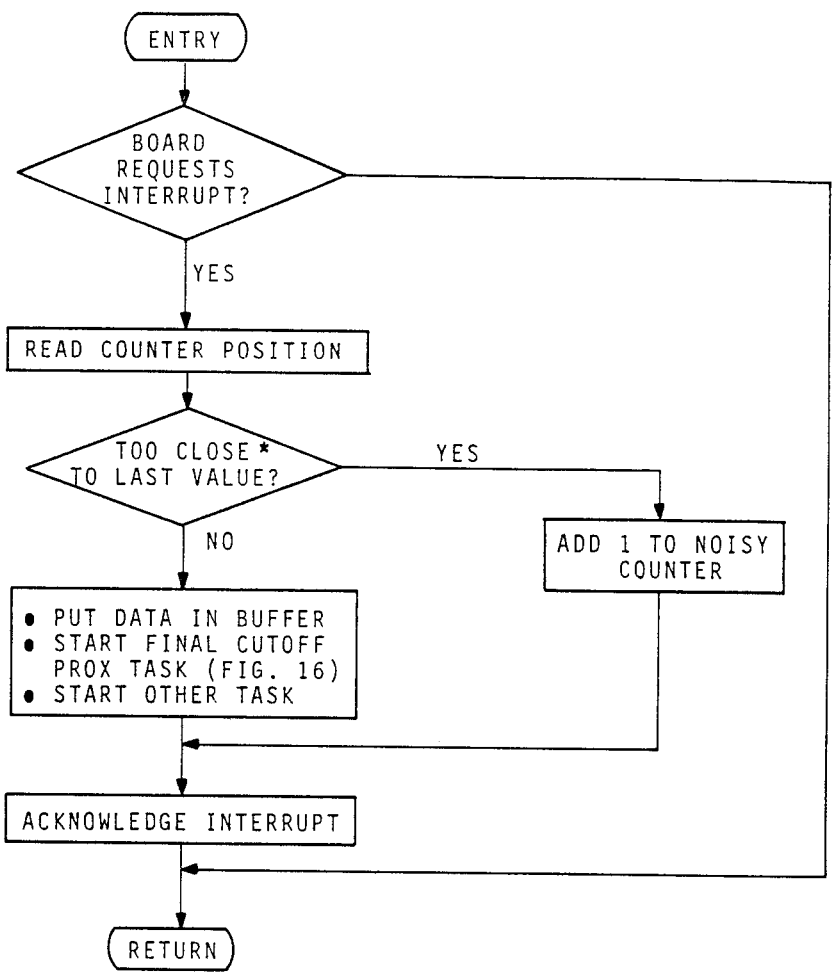
FIG. 15 is a flow diagram which shows a representative final cutoff proximity switch interrupt service routine.

A further routine employed in the practice of the present invention is a final cutoff proximity interrupt service routine. A flow diagram of which is representatively shown in FIG. 15. This interrupt routine reads counter data and checks for spurious pulses. The routine then places signal data from proximity switch 52 into a buffer, and initiates the final cutoff proximity switch data processing routine.

Figure 16:
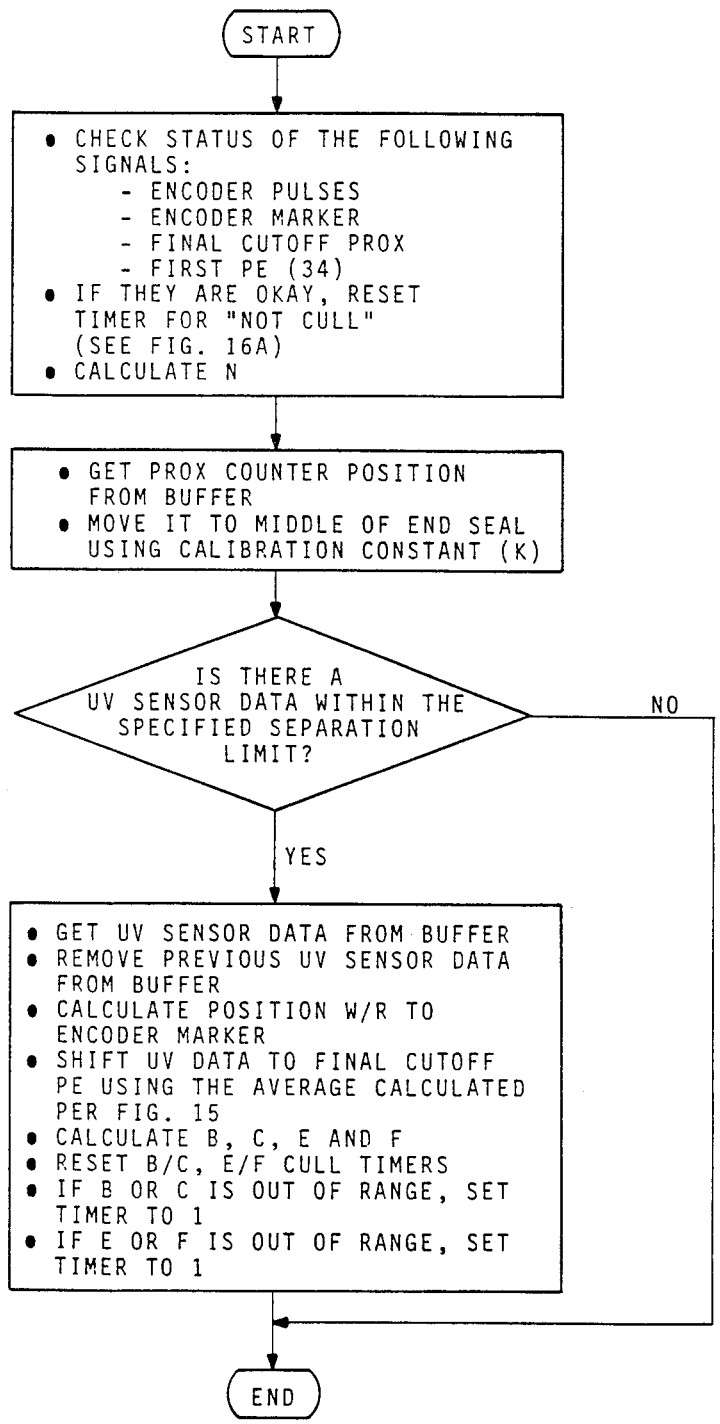
FIGS. 16 and 16A are block flow diagrams which show a representative final cutoff proximity switch data processing routine.
Figure 16A:
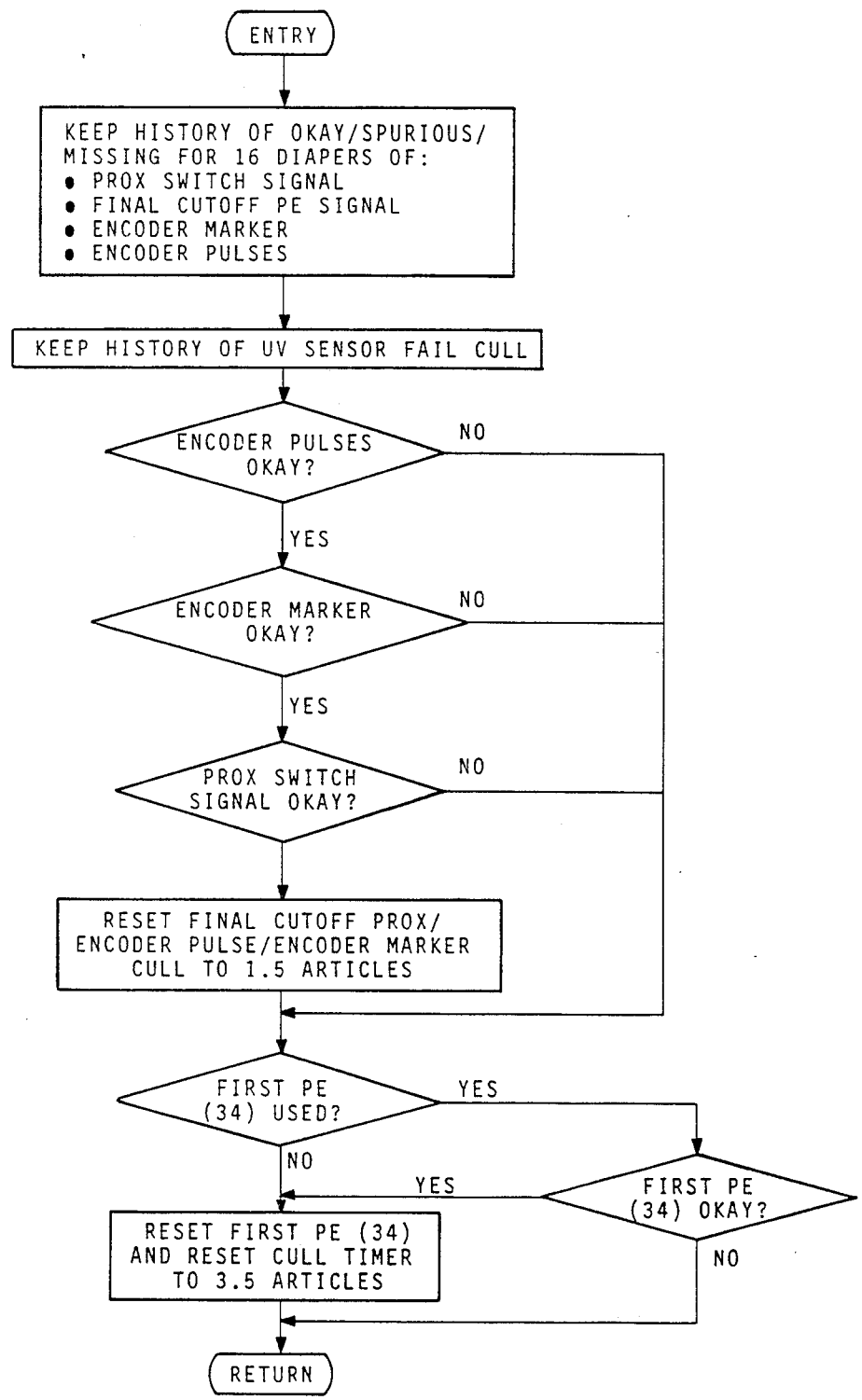

A flow diagram of the proximity switch data processing routine is representatively shown in FIGS. 16 and 16A. The proximity switch data processing routine checks the status of the various detectors and sensors and adjusts the proximity switch data with a calibration constant to generate data corresponding to the middle of the end seal. The middle of the end seal corresponds to a machine-direction distance approximately halfway between consecutive pads 16. The processing routine then recalls UV detector data from its location in the storage buffer and discards previous, noncurrent UV detector data. The newly recalled UV detector data is then combined with data from photoeye 36 and with data from proximity switch 52 to calculate "B", "C", "E" and "F" (FIG. 7B). "B" and "C" are encoder phase pulse counts corresponding to distances 86 and 88, respectively, and "E" and "F" are phase pulse counts corresponding to distances 90 and 92, respectively (FIG. 8). The values for "B", "C", "E" and "F" are checked against predetermined acceptance value ranges, and if they are out of their respective ranges, the particular article is identified for culling. In addition, this routine calculates "N", which is a number of encoder phase pulse counts between the "component reference" for a selected operational element, such as the waist elastic applicator, and the "function reference" for that operational element. In the described embodiment of the invention, the "component reference" is a signal corresponding to an edge of a pad 16, and the "function reference" is a signal corresponding to an actual mechanical operation of placing a waist elastic member 20 onto web 10.

Figure 17:
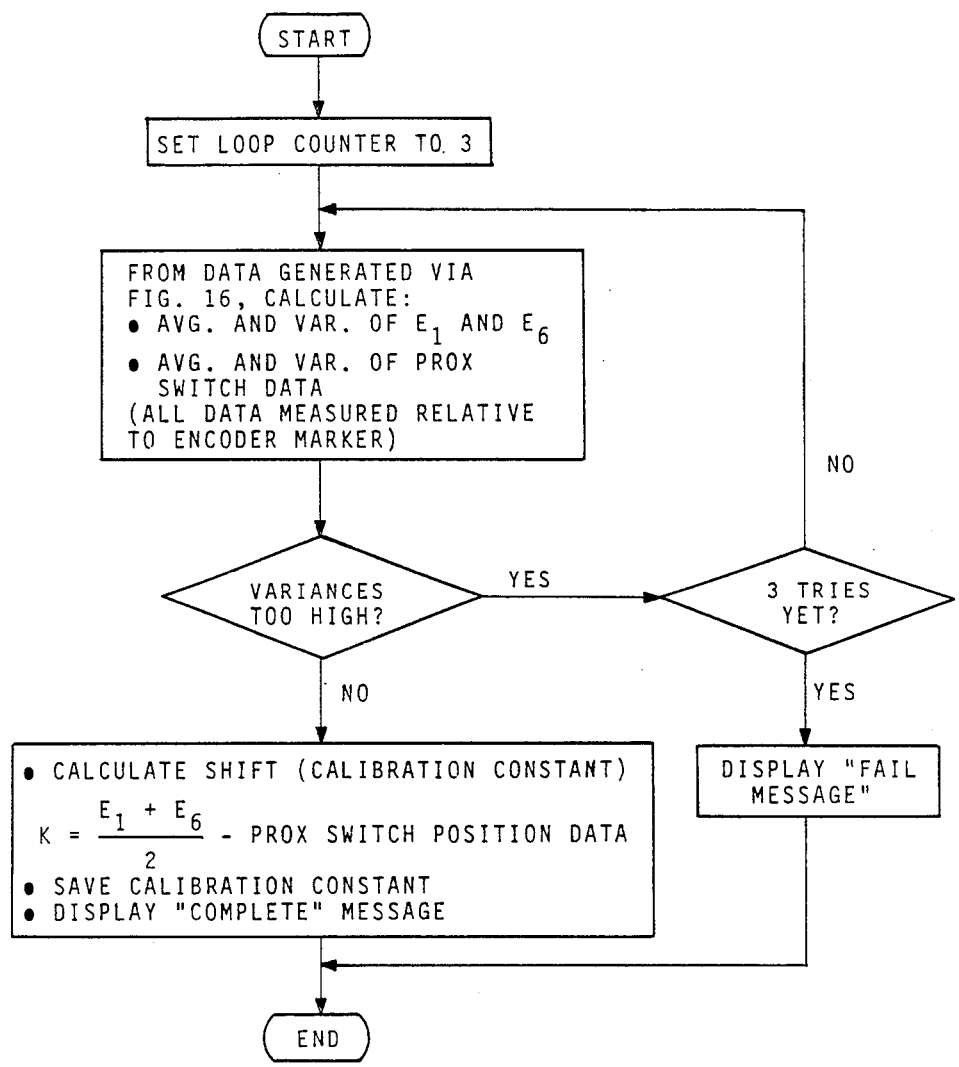
FIG. 17 is a flow diagram which shows a representative calibration routine.

A flow diagram for the calibration routine employed with the present invention is representatively shown in FIG. 17. In the illustrative embodiment, the calibration routine begins when the operator presses an appropriate key on a control panel. Once the routine is initiated, data from the proximity switch processing routine (FIG. 16) is employed to calculate average position values corresponding to the locations of edges E1 and E6. In addition, the routine calculates a value corresponding to the average position of the data from proximity switch 52. The position values for E1, E6 and the proximity switch signal are all determined relative to a corresponding marker pulse 70. The calibration routine then calculates a calibration constant employing the following formula:

$$K = \frac{E1 + E6}{2} - PS$$

Where:
K = calibration constant
E1 = pulse position value for edge E1
E6 = pulse position value for edge E6
PS = pulse position value for proximity switch signal.

In addition to the culling function described above, the method and apparatus of the invention can be constructed and arranged to more accurately control the mechanical operation of placing selected structural members onto web 10. In addition, the invention can be arranged to control the configuration of other web components, such as the end seal lengths and the cutoff location between individual articles. For example, with reference to FIG. 8, the method and apparatus of the present invention can advantageously be employed to selectively regulate and adjust the placement of waist elastic members 20a and 20b on web 10. In particular, the invention can include means for regulating an elastic applicator employing a data signal from a registration control means, such as a waist elastic registration control loop.

A formula for controlling a set point (SP) of the waist elastic registration control loop is as follows:

New SP = delayed $\overset{\ominus}{\overline{N}}$ + (D − A)/2

"SP" is data represented by a target number of encoder phase pulse counts which "N" is desired to equal.

"New SP" is a "SP" which has been suitably adjusted to make "A" = "D".

"$\overline{N}$" correspond to an old, previous set point, and in the shown embodiment, is the running average of the number of encoder phase pulse counts between the "component reference" for the elastic waist applicator and the "function reference" for the elastic waist applicator.

"Delayed $\overline{N}$" is "$\overline{N}$" held or otherwise delayed by a value corresponding to the distance between the function reference detector and the UV detector 40. A suitable delaying means is, for example, a storage buffer in computer 50. The purpose of this delay is to match selected "function reference" data signal with its properly corresponding "component reference" data signal, and thereby ensure that the two signals relate to the same article 12. Thus, "delayed $\overline{N}$" is a phase pulse count derived from properly matched "component reference" and "function reference" signals. The above-described step of producing the "delayed $\overline{N}$" value can provide a more accurate determination of the proper set point and can advantageously increase the accuracy and reliability of the inspection and culling operations provided by the invention.

"A" and "D" are the values of encoder counts between pad 16 and a corresponding, adjacently located waist elastic member 20. "A" corresponds to spacing distance 82, and "D" corresponds to distance 84.

To automatically control the placement of waist elastic members 20a–b, the values for "A" and "D" are continually gathered by computer 50. Under desired conditions, the values for "A" and "D" are the same. If they are not the same, then the set point for the waist elastic control loop is automatically determined and adjusted employing the above-mentioned formula.

Figure 18:
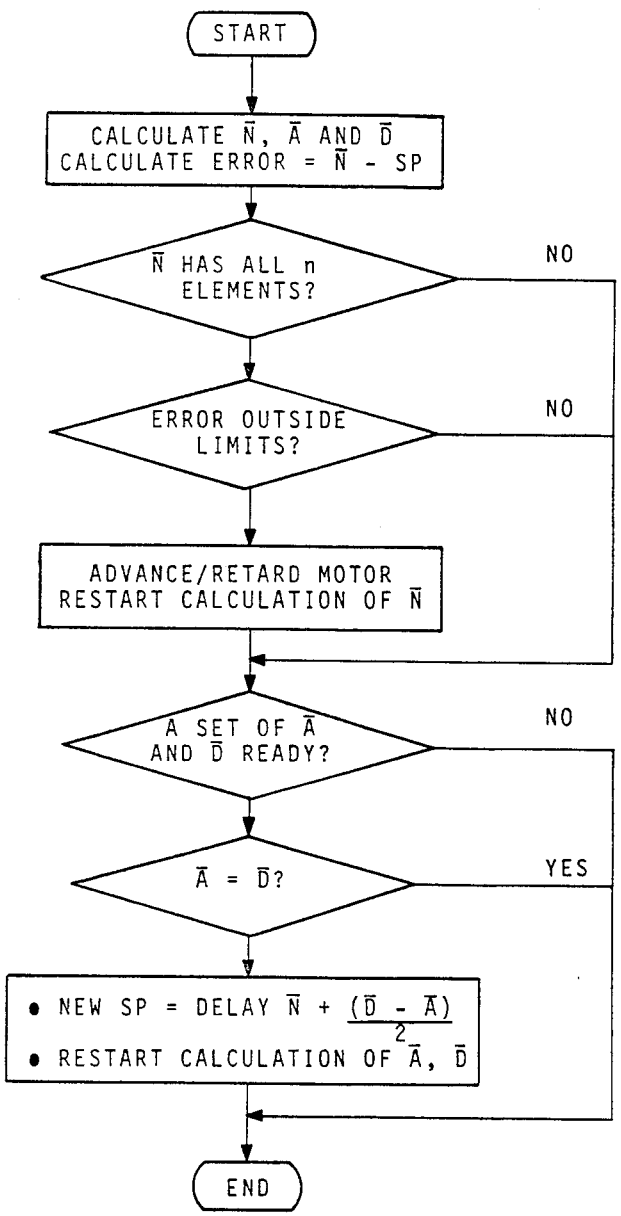
FIG. 18 is a flow diagram which shows a representative control routine.

A block flow diagram of a representative control routine is illustrated in FIG. 18. In the illustrated embodiment, the control routine operates to keep "N" near a predetermined set point and to adjust the set point to make $\overline{A}=\overline{D}$. "N" is a particular number of encoder phase pulse counts observed between the "component reference" and the "function reference". "$\overline{N}$" is again the average of "N", and "n" is the number of individual values employed to calculate "$\overline{N}$". "$\overline{A}$" and "$\overline{D}$" are averages of position pulse counts corresponding to distances 92 and 90 (FIG. 8).

The illustrated embodiment of the control routine employs the current SP value to generate an error signal value. If the error value is outside a predetermined limit, a signal is generated to advance or retard the relative phasing of a waist elastic applicator relative to the moving web 10 and thereby adjust the locations of the waist elastics relative to the respective end edges of corresponding pads 16.

More particularly, as representatively shown in FIG. 1A, signal data from the registration control routine is routed to a regulating means 94 for appropriately adjusting the phasing of the waist elastic applicator (not shown). Regulating means 94 comprises a stepper motor, such as a SUPERIOR ELECTRIC Model DRD 004 and associated electronics manufactured by the Superior Electric Company located in Bristol, Conn.; and a variable ratio gear box, such as a SPECON Model No. 4 PSD 100 phase shifting differential transmission manufactured by Fairchild Industrial Products Company located in Winston-Salem, N.C. The regulating means is connected and arranged in a conventional manner known in the art to selectively and operatively advance or retard the position at which the waist elastic applicator mechanism places and affixes the individual elastic members onto the moving web. For example, a suitable waist elastic applicator is described in U.S. Pat. No. 4,608,115 issued Aug. 26, 1986 to C. Schroth, et al., which is hereby incorporated by reference thereto. In such embodiment of the invention, the stepper motor and variable ratio gear box are operably connected to accelerate or decelerate the rotation of the rotatable carrier drum for a suitable, limited period of time to thereby index and adjust the relative phasing between the web and the individual applicator mechanisms carried by the drum, as desired.

Having thus described the invention in rather full detail, it will be readily apparent that various changes and modifications can be made without departing from the spirit of the invention. All of such changes and modifications are contemplated as being within the scope of the invention, as defined by the subjoined claims.

We claim:

1. An apparatus for examining a web, which includes an interconnected plurality of articles, to determine a location of a selected component thereof, comprising:
    indicating means for providing marker data corresponding to the presence of a selected article;
    metering means for generating gauge data corresponding to selected incremental lengths of said article along a movement direction of said web;
    first designating means for providing first reference data corresponding to a selected reference point on said article;
    locating means for detecting location data corresponding to a position of a selected component of said article;
    first evaluating means for processing said first reference data, said location data and said gauge data to determine first spacing data corresponding to a spaced distance between said component and said reference point;
    second designating means, which is spaced from said first designating means, for providing additional, updated reference data corresponding to said selected reference point on said article;
    second evaluating means for processing said first spacing data and said updated reference data to determine updated spacing data corresponding to said component and said reference point;
    comparator means for determining a difference between said updated spacing data and a predetermined acceptance spacing range; and
    culling means for identifying selected articles for which said updated spacing data is outside of said acceptance spacing range.

2. An apparatus as recited in claim 1, wherein said locating means for detecting position data comprises:
    irradiating means for exposing said component to a source of UV radiation to induce an emission of a selected radiation spectra from said component;
    receptor means for detecting said emitted radiation spectra.

3. An apparatus as recited in claim 1, wherein said first designating means comprises a photoeye.

4. An apparatus as recited in claim 1, further comprising calibrating means for establishing shift data which provide for a separation of said web at a selected spaced distance from said reference point.

5. An apparatus as recited in claim 1, further comprising adjustment means for regulating a positioning of a selected component on said web.

6. An apparatus as recited in claim 1, further comprising delaying means for matching selected function reference data with properly corresponding component reference data.

7. An apparatus as recited in claim 1, wherein said first designating means comprises a UV detector.

8. An apparatus as recited in claim 1, further comprising registration control means for automatically determining set point data corresponding to a desired location of said selected component.

9. An apparatus as recited in claim 1, further comprising regulating means for adjusting a relative phasing between a selected operational element and said web.

10. An apparatus as recited in claim 9, wherein said operational element is a waist elastic applicator.

11. An apparatus as recited in claim 1, wherein said first designating means comprises a UV detector and said second designating means comprises a photoeye.

12. An apparatus as recited in claim 1, wherein said first designating means comprises a first detector and a second detector for producing a composite signal.

13. An apparatus as recited in claim 1, wherein said second evaluating means includes delaying means for matching said updated reference data with properly corresponding first reference data and properly corresponding position data.

14. An apparatus as recited in claim 13, wherein said second evaluating means provides an average phasing shift value for matching said updated reference data with properly corresponding first reference data and properly corresponding position data.

15. An apparatus as recited in claim 13, wherein said delaying means is a storage buffer in a computer.

16. An apparatus as recited in claim 1, further comprising triggering means for producing data corresponding to a separating of said web at a selected distance from said reference point.

17. An apparatus as recited in claim 16, wherein said triggering means includes means for offsetting a phasing of a proximity switch signal to provide accurate data regarding said separating of said web.

18. An apparatus as recited in claim 1, further comprising means for detecting an area of said article which is deficient of material.

19. An apparatus as recited in claim 1, further comprising means for culling articles for which reference data or position data are missing.

20. A method for examining a web, composed of an interconnected plurality of articles, to determine a location of a selected component thereof, comprising the steps of:
 (a) marking the presence of a selected article;
 (b) metering gauge data corresponding to selected incremental lengths of said article along a movement direction of said web;
 (c) designating first reference data corresponding to a selected reference point on said article;
 (d) sensing location data corresponding to a position of a selected component of said article;
 (e) evaluating said first reference data, said location data and said gauge data to determine first spacing data corresponding to a relative distance between said component and said reference point;
 (f) providing additional, updated reference data corresponding to said selected reference point on said article, said updated reference data being provided at a position spaced from said designating step (c);
 (g) processing said first spacing data and said updated reference data to determine updated spacing data corresponding to said component and said reference point;
 (h) comparing said updated spacing data with a predetermined acceptance spacing range; and
 (i) culling selected articles for which said updated spacing data is outside of said acceptance spacing range.

21. A method as recited in claim 20, wherein said designating step (c) comprises the step of producing data with a photoeye.

22. A method as recited in claim 20, wherein said designating step (c) comprises the step of producing data with a UV detector.

23. A method as recited in claim 20, wherein said designating step (c) comprises the step of producing data with a UV detector and said providing step (f) comprises the step of producing said updated reference data with a photoeye.

24. A method as recited in claim 20, wherein said designating step (c) comprises the step of producing data with a first detector and a second detector which produce a composite signal.

25. A method as recited in claim 20, wherein said processing step (g) includes the step of matching said updated reference data with properly corresponding first reference data and properly corresponding position data.

26. A method as recited in claim 25, wherein said matching step comprises the step of storing said function reference data in a computer buffer.

27. A method as recited in claim 20, wherein said processing step (g) includes the step of providing an average phasing shift value for matching said updated reference data with properly corresponding first reference data and properly corresponding position data.

28. A method as recited in claim 20, further comprising the step of producing data corresponding to a separating of said web at a selected distance from said reference point.

29. A method as recited in claim 20, further comprising the step of offsetting a phasing of a proximity switch signal to provide accurate data regarding said separating of said web.

30. A method as recited in claim 20, further comprising the step of detecting an area of said article which is deficient of material.

31. A method as recited in claim 20, further comprising the step of culling articles for which reference data or position data are missing.

32. A method as recited in claim 20, further comprising the steps of:
 generating cutoff data corresponding to a location at which said selected article is separated from an adjacent article in said web; and
 separating said web at said cutoff location.

33. A method as recited in claim 32, wherein said step of sensing position data comprises the steps of:
 exposing said component to a source of UV radiation to induce an emission of a selected spectra of radiation from said component; and
 detecting said emitted radiation spectra.

34. A method as recited in claim 20, further comprising the step of matching selected function reference data with properly corresponding component reference data.

35. A method as recited in claim 20, further comprising the step of automatically determining set point data corresponding to a desired location of said selected component.

36. A method as recited in claim 20, further comprising the step of adjusting a relative phasing between said web and a selected operational element.

37. A method as recited in claim 36, wherein said adjusting step comprises the step of adjusting the operation of a waist elastic applicator.

* * * * *